US007699821B2

(12) United States Patent
Nowak (10) Patent No.: US 7,699,821 B2
(45) Date of Patent: Apr. 20, 2010

(54) MULTI-FUNCTIONAL PORT

(75) Inventor: Piotr Nowak, Muenster (DE)

(73) Assignee: Covance Laboratories GmbH, Muenster (DE)

( * ) Notice: Subject to any disclaimer, the term of this patent is extended or adjusted under 35 U.S.C. 154(b) by 1254 days.

(21) Appl. No.: 10/798,450

(22) Filed: Mar. 12, 2004

(65) Prior Publication Data

US 2005/0203484 A1 Sep. 15, 2005

(51) Int. Cl.
*A61M 37/00* (2006.01)
(52) U.S. Cl. .................... 604/288.02; 604/502
(58) Field of Classification Search ..................
604/288.01–288.04, 891.1, 502, 500
See application file for complete search history.

(56) References Cited

U.S. PATENT DOCUMENTS

| 3,910,283 | A | * | 10/1975 | Leveen ............................. 604/9 |
| 4,430,081 | A | * | 2/1984 | Timmermans ............... 604/256 |
| 4,781,695 | A | * | 11/1988 | Dalton ........................ 604/175 |
| 4,790,826 | A | | 12/1988 | Elftman |
| 4,886,501 | A | | 12/1989 | Johnston et al. |
| 4,915,690 | A | | 4/1990 | Cone et al. |
| 5,053,013 | A | | 10/1991 | Ensminger et al. |
| 5,120,317 | A | | 6/1992 | Luther |
| 5,263,930 | A | * | 11/1993 | Ensminger ............. 604/288.03 |
| 5,738,660 | A | | 4/1998 | Luther |
| 5,762,636 | A | | 6/1998 | Rupp et al. |
| 5,848,989 | A | | 12/1998 | Villani |
| 6,210,366 | B1 | | 4/2001 | Sanfilippo, II |

FOREIGN PATENT DOCUMENTS

| AU | 7813498 | 12/1998 |
| DE | 196 24 320 C 1 | 6/1997 |
| EP | 0 332 943 A1 | 9/1989 |
| EP | 0 343 910 A2 | 11/1989 |
| EP | 0 474 266 A2 | 3/1992 |
| WO | WO 98/55167 | 12/1998 |

OTHER PUBLICATIONS

"The Facts About Intravenous Catheter Lines", A fact sheet from Seattle Treatment Education Project, Oct. 1992, posted at The Body Apr. 1996, pp. 1-4.
CPT Coding for Central Venous Access_Types of Devices, pp. 1-2.
K. Soontornvipart, et al, "Review Article, Effects of Metallic Implant on the Risk of Bacterial Osteomyelitis in Small Animals", Department of Surgery, Orthopaedics and Radiology, Small Animal Clinic, Faculty of Veterinary Medicine, University of Veterinary and Pharmaceutical Sciences, Brno, Czech Republic, ACTA VET. BRNO 2003, 72:, pp. 235-247.
"Access Catheter: Port-A-Cath", 1999, WB Saunders Company, pp. 5-6.

* cited by examiner

*Primary Examiner*—Nicholas D Lucchesi
*Assistant Examiner*—Theodore J Stigell
(74) *Attorney, Agent, or Firm*—McDermott Will & Emery LLP (57) ABSTRACT

A subcutaneous port includes an elongated port corpus having a proximal end defining a septum receiving opening angled in relation to a longitudinal axis of said port corpus, a substantially cylindrical body, and a substantially frustoconical conus having an outlet opening provided at a distal end thereof. The cylindrical body defines a chamber along at least a portion of a length thereof and the cylindrical body and frustoconical conus collectively define a passage to permit passage of fluid between the chamber and the outlet opening. A septum is retained in the septum receiving opening by a septum retainer. A catheter is connected to the port corpus passage.

28 Claims, 10 Drawing Sheets

| SPECIES / INFUSION AND SAMPLING | MOUSE | RAT | RABBIT | GUINEA PIG | FERRET |
|---|---|---|---|---|---|
| SUBCUTANEOUS | ● | ● | ● | ● | ● |
| INTRAPERITONEAL | ● | ● | ● | ● | ● |
| INTRA VENOUS INF. | ● | ● | ● | ● | ● |
| INTRA ARTERIAL INF. | ● | ● | ● | ● | ● |
| INTRA THECAL INF. | | | ● | | |
| INTRA VENTRICULAR INF. | | | ● | | |
| BLOOD SAMPLING | | ● | ● | ● | ● |

FIG. 10

MULTI-FUNCTIONAL PORT

TECHNICAL FIELD

The disclosure relates generally to implantable ports. The disclosure relates more particularly to a catheterizable, multi-functional subcutaneous port utilizing a self-sealing septum for delivery and/or collection of drugs and/or bodily fluids and an implantation method.

BACKGROUND

Intravascular catheters, such as that disclosed in U.S. Pat. No. 5,762,636, have commonly been used for repeated drug administration and/or blood sampling on animals such as mice, rats, rabbits, dogs, cats, sheep, and human and non-human primates. However, the use of intravascular catheters in such applications, particularly for repeated drug administration over a period of time, poses an unacceptably high risk of infection of the open wound and of catheter disengagement and/or damage caused by movement or actions of the animal.

In extended use applications, it is therefore preferable to use surgically implanted ports as a means of delivering drugs or collecting bodily fluids. Subcutaneous ports generally comprise a housing defining a chamber, a septum disposed with one surface adjacent the dermis and an opposing surface adjacent the chamber, and an output. The chamber communicates with a delivery and/or collection site in the patient or subject through the output, which often includes a catheter.

Once the port is implanted and the chamber filled with a drug, a bolus or therapeutic dose of the drug contained in the chamber is delivered at a desired rate to a particular location within a patient's or subject's body, such as a cavity, a large vein, a tumor, or an injury site. The septum comprises an elastomeric material that is penetrable by a needle and is self-sealing to mitigate the leakage that would otherwise result from repeated punctures from injections or fluid collection. The chamber may be replenished by inserting a hypodermic needle through the patient's or subject's skin and the septum and injecting the drug into the chamber.

Ports therefore permit a means for efficiently dispensing a drug or medicament into the body of a patient or subject over a prolonged period of time by means of a single injection (e.g., continuous infusion) or repeated intermittent injections. Likewise, ports offer the opportunity for collection of fluids (e.g., blood) from a designated collection site adjacent an outlet of a catheter attached to the port. For example, with respect to dogs and cats, a catheter attached to the port may used to sample blood from the cephalic, recurrent metatarsal, jugular, and femoral veins. However, sampling is feasible, but generally not advisable, for small needles (e.g., 22-gauge) due to the potential for plugging or occlusion of the needle. Sampling using needles of 20-gauge, 18-gauge, or large is generally acceptable. Despite the real advantages provided by implantable ports, conventional ports suffer from numerous disadvantages, some of which are described below with respect to two conventional ports.

U.S. Pat. No. 5,848,989 provides one example of an implantable port for delivering and collecting fluids in a body particularly for use with laboratory animals. This port has a hollow housing 2 in which a relatively small inlet 7 is defined by a radially inwardly projecting lip 18 which is substantially perpendicular to the base 17 of the housing. A septum 4 is mounted in the housing adjacent a mouth of the inlet and is then compressed against the housing inlet lip 18 by a hollow core 3 inserted within the housing in a compression fit. The housing 2 has an open flared end 5 extending in front of the inlet 7 and having a surface shaped to guide a needle to the port inlet and into the septum.

However, this configuration presents many disadvantages including a prismatic shape which both resists manual fixation and presents edges which can damage tissue if the edges are pressed against the surrounding tissue during manual fixation prior to insertion of a needle. Moreover, the septum is obscured by the inlet lip and, in combination with open flared end of the housing which serves to guide a needle to the inlet 7 during use, the risk of damage to the needle tip upon initial needle insertion is significant. Further, once the septum is penetrated, the required angle of insertion is likely to cause the needle tip to immediately impact against an interior wall of the hollow core 3 chamber 8. Each needle insertion therefore presents a hazard during both needle insertion and needle withdrawal, as the damaged needle tip cuts lesions or tears into the septum. Another hazard is presented as the needle outer diameter increases relative to the septum diameter.

Such tears and lesions provide an ideal environment for the growth of bacteria in the subcutaneous environment, increase the risk of infection and/or tissue necrosis, and increase leakage from the septum. These factors reduce the useful life of the port and may necessitate an additional surgical procedure to removal the damaged port and insert a new port, with the attendant risks of infection and trauma to the animal and possibly loss of test data. In practice, the interference fit between the housing 2 and the hollow core 3 renders disassembly and reassembly of the port to replace septum 4 during surgery highly impractical at the very least and the entire port replaced.

An additional disadvantage in the device disclosed in U.S. Pat. No. 5,848,989 arises from the asymmetric geometry and angles surfaces (e.g., corners) presented thereby. When any port is implanted in a body, fibroblasts lay down dense fibrous tissue (collagen, elastin, reticular) in reaction to the foreign body so as to isolate the foreign body. The material and shape of the foreign body influences the thickness of the fibrous capsule (encapsulation). The asymmetric shape of the aforementioned device with a relatively larger inlet end, the presence of the septum at the inlet end, the repeated punctures of the septum (and formation of lesions therein), and repeated punctures of the fibrous capsule all contribute to a disproportionate encapsulation or fibrosis (scar tissue formation) at the front or inlet end. Over time, this disproportionate encapsulation causes migration of the port away from the original site in a direction of the outlet, particularly when absorbable sutures are used. Migration of the port may cause the catheter to kink or bend causing occlusion and/or damage, particularly for small diameter catheters (e.g., French size 3 or 4, having an outer diameter of about 0.9 mm and 1.20 mm, respectively).

German Patent No. 0474266 provides another example of an implantable catheter device for a small experimental animal characterized a tubular housing 10 having a cavity 13 closed at an end face thereof by a penetrable septum 14. The other end area of the housing 10 forms a connection part 30 in which a clamping space 21 receives an elastomeric clamping piece 11 surrounding a catheter 12. A portion of the connection part 30 projecting beyond clamping piece 11 has internal threads 31 matingly engageable with an external thread of pressure piece 20 shaft 32. The end face of the externally threaded shaft 32 axially compresses clamping piece 11 to press it against catheter 12 provided on a rigid supporting cannula 22. The cannula's lumen communicates with the cavity 13, on one side, and the pressure piece 20 and associated catheter 12 on the other side.

However, similar to the device of U.S. Pat. No. 5,848,989, the retaining ring 15 flange 16 of this port defines a small septum target area, relative to the outside diameter of the port housing, that is inwardly displaced from the outer edge of the flange. This configuration presents an increased risk for needle damage and associated complications, as noted above. Further, the minimal cavity 13 depth, combined with the required angle of needle insertion, provides an almost imperceptible clearance for a needle the tip between the septum inner wall and the cavity 13 wall, increases the probability of damage to the needle tip upon insertion and damage to the septum upon withdrawal of the needle. Additionally, if the integrity of the septum is compromised, the connection part 30 and the retaining ring 15 welded thereto must be removed and discarded.

Thus, a need exists for an implantable subcutaneous port which avoids the above-noted deficiencies of conventional subcutaneous ports.

SUMMARY

In accord with the present disclosure, a subcutaneous port comprises a port corpus, a septum, a removable septum retainer, and a removable conus. The port corpus is elongated about an axis and comprises an inlet defining an opening at one end of the port corpus, an outlet having an outlet opening at a lengthwise opposing end of the port corpus, and a chamber defined therebetween. The inlet or the inlet opening comprises a first connecting member and the outlet or the outlet opening comprises a second connecting member. The removable septum retainer comprises a third connecting member being removably engaged with the first connecting member so as to dispose the septum in a position to occlude the port corpus inlet opening. The removable conus extends along the axis and comprises an inlet end having an inlet opening at one end of the removable conus, an outlet connector having an outlet opening at an opposing lengthwise end of the removable conus, and a channel extending therebetween. The removable conus inlet end further comprises a fourth connecting member being removably engaged with the second connecting member. The port corpus inlet opening is canted inwardly along the axis of the port corpus.

Also provided are methods for preparing for implantation a subcutaneous port in accord with the above example and a surgical procedure for implanting such a subcutaneous port in an animal. The former method comprises selecting a port corpus, a removable septum retainer, a septum, a removable port conus, and a catheter for assembly, disposing the septum between the port corpus inlet opening and the removable septum retainer to occlude an inlet opening of the port corpus, connecting the removable septum retainer to the port corpus by connecting the first connecting member to the third connecting member, connecting the removable conus to the port corpus by connecting the fourth connecting member and the second connecting member, and connecting the catheter to the removable conus outlet connector. The noted surgical procedure comprises the steps of making an incision in the skin of the animal, inserting the subcutaneous port beneath the skin, positioning a distal end of the catheter at a predetermined site within the animal, and closing the incision.

Another aspect of a subcutaneous port in accord with the present concepts includes a fifth connecting member provided adjacent an exterior surface of one of the removable conus and the port corpus and a removable hollow casing extending along the axis, the removable hollow casing comprising a sixth connecting member being removably engaged with the fifth connecting member. The method for preparing for implantation of this aspect of a subcutaneous port comprises, further to the above noted method, connecting a removable hollow casing to the removable conus by screwing the fifth connecting member and the sixth connecting member together. A surgical procedure for implantation of the subcutaneous port into an animal includes making an incision in the skin of the animal, inserting the subcutaneous port beneath the skin, positioning a distal end of the catheter at a predetermined site within the animal, and closing the incision.

Another method in accord with the disclosed concepts includes a method for implanting an elongate subcutaneous port into a rodent includes the steps of making a longitudinal and/or a transverse incision in the skin of the rodent in a generally posterior dorsal location with at least a portion of the incision disposed adjacent a base of the tail, inserting the subcutaneous port beneath the skin with a septum borne by the elongate subcutaneous port being disposed adjacent the base of the tail, positioning a distal end of a catheter borne by the elongate subcutaneous port at a predetermined site within the animal, and closing the incision.

In another aspect, a subcutaneous port is provided including an elongated port corpus having a proximal end defining a septum receiving opening angled in relation to a longitudinal axis of the port corpus, a substantially cylindrical body, and a substantially frustoconical conus having an outlet opening provided at a distal end thereof, the substantially cylindrical body defining a chamber along at least a portion of a length thereof and the substantially cylindrical body and the substantially frustoconical conus collectively defining a passage to permit passage of fluid between the chamber and the outlet opening, a septum provided in the septum receiving opening; a septum retainer for retaining the septum in the port corpus; and a catheter connected to the port corpus passage.

Additional aspects of the present disclosure will become readily apparent to those skilled in the art from the following detailed description, wherein various general aspects of the invention are described by way of illustrative examples.

DETAILED DESCRIPTION

Figure 1A:
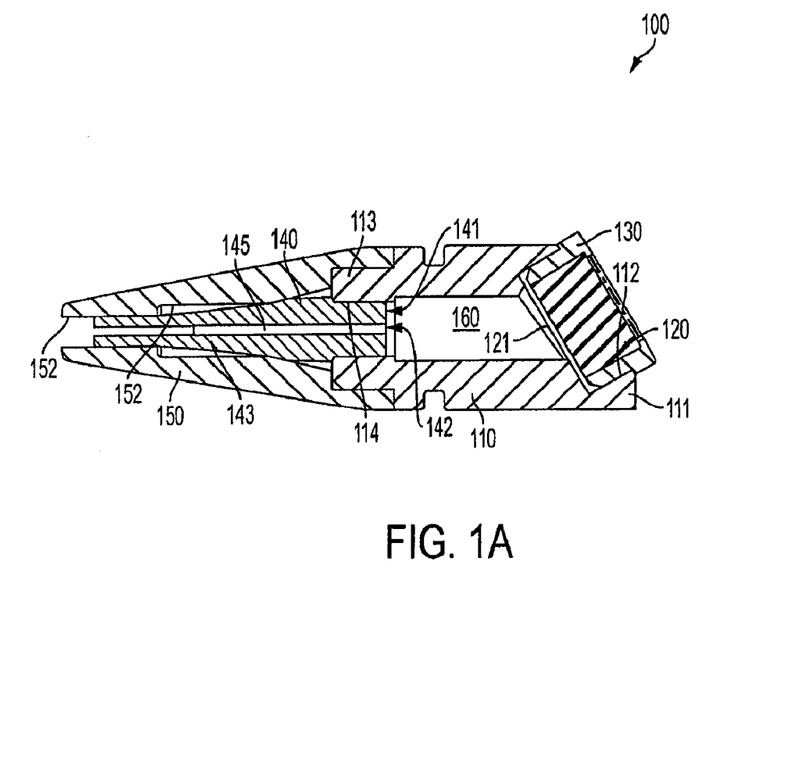
FIGS. 1(a)-1(b) respectively show a cross-sectional view of an example of an implantable subcutaneous port in accord with the present concepts and a representation of such implantable subcutaneous port in an implanted position.
Figure 1B:
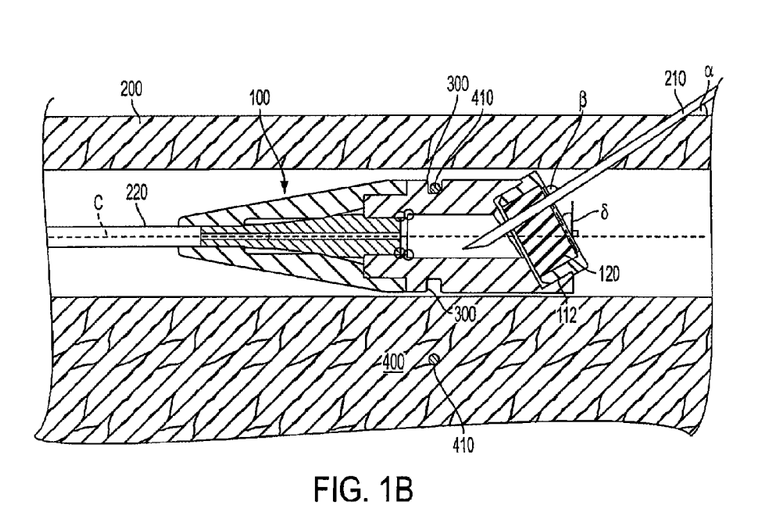

FIGS. 1(a)-(b) show cross-sectional views of an example of an implantable subcutaneous port 100 in accord with the present concepts. In the illustrated example, the subcutaneous port 100 comprises port corpus 110, a septum 120, a removable septum retainer 130, a port conus 140, and a removable hollow casing 150.

Figure 2:
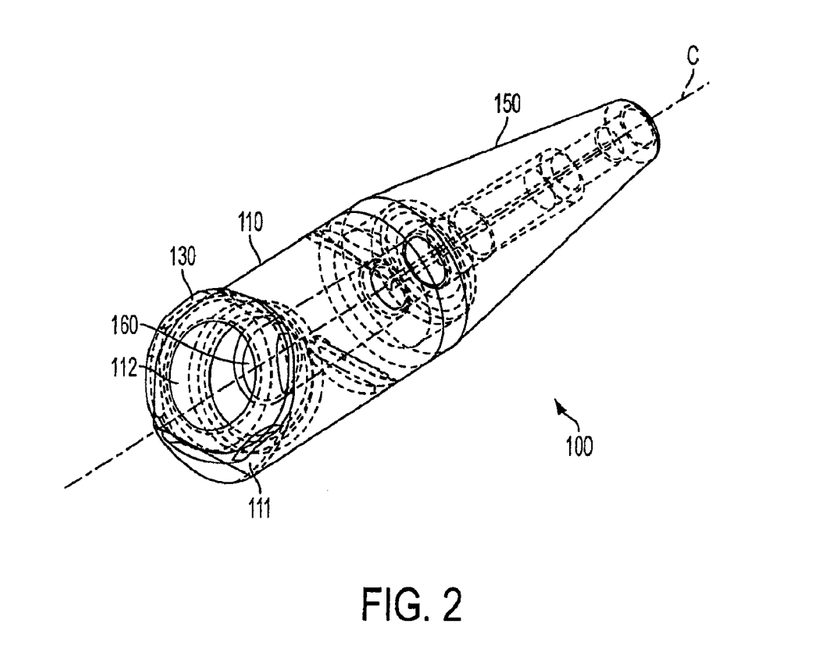
FIG. 2 shows an isometric view of a subcutaneous port in accord with the example of FIGS. 1(a)-(b).

The overall profile of the subcutaneous port 100, shown by way of example in FIG. 2, comprises a substantially cylindrical port corpus 110 and a substantially frustoconical removable hollow casing 150. Port corpus 110 has an outer surface which is substantially cylindrical along an axis of the port corpus (e.g., center axis C) and hollow casing 150 is frustoconical along a portion of its length along the axis. The outer surfaces of the port corpus 110 and the removable hollow casing 150 are preferably smooth and curved, being substantially curvilinear in a cross-section taken along the axis. In one aspect, an outer surface of each of the port corpus 110 and the removable hollow casing 150 substantially circular or substantially elliptical in a cross-section taken along the axis.

Subcutaneous port 100 is particularly suited for use with humans or with experimental animals or domestic animals such as mice, rats, rabbits, dogs, cats, sheep, and primates, or any other experimental, domestic or feral animal, to facilitate continuous or intermittent drug and/or fluid administration and/or blood sampling therefrom. The slender profile of subcutaneous port 100 offers, among other advantages, greater flexibility in installation of the port in rodents (e.g., rats, mice) and permit installation of the port in a posteriorally disposed location (e.g., dorsal or lateral), such as near the base of the tail. Dorsal or substantially dorsal placement is preferred for rodents. A purely lateral or purely ventral placement is not generally recommended, but could be realized in accord with the presently disclosed subcutaneous port to facilitate special circumstances or cases. The slender profile of subcutaneous port 100 also permits secure and efficient fixation of the port during needle insertion (e.g., piercing of the membrane), as the forces generated during needle insertion are substantially offset by the forces generated by the person manipulating the port and are therefore not transmitted to sensitive or vital organs (e.g. heart, lung). Moreover, once a connection between a needle and the subcutaneous port 100 has been made, the shape of the port chamber as well as the angle between membrane and needle guarantee a stable connection. Additionally, slender profile of subcutaneous port 100 permits elimination of the need for neck grip fixation of the animal when application tubes are utilized. In contrast, conventional ports are typically installed in the vicinity of the rodent's neck (e.g., (catheterization of the v. jugularis ext.), where pressure from manual fixation and needle insertion exerts heavy pressure on the thorax and fixation of the rat through a neck grip may displace the catheter, which poses a danger of accidental heart tamponade, or damage the connection between the catheter and the port.

In the implanted position shown in FIG. 1(b), the septum 120 is disposed so that an outer surface thereof is adjacent the dermis 200. The septum 120 and the associated port corpus inlet opening 112 is canted inwardly along the axis of the port corpus at an angle $\delta$, which angle may be measured with respect to a center axis C of the subcutaneous port 100 or any arbitrary axis parallel thereto. Although angle $\delta$ may range between 0° and 90°, non-inclusive, the port corpus inlet opening 112 is advantageously canted inwardly with respect to an axis of the port corpus (e.g., center axis C) within a range between 20° and 70° and, still more preferably, between 40° and 60°.

The aforementioned placement of the septum permits a needle 210 inserted at an angle $\alpha$ to the dermis 200 to pierce the septum at a favorable angle $\beta$. Angle $\alpha$ may generally range from about 10° to 60°, with smaller angles of attack within this range being preferable for the needle tip. Angle $\beta$ may be 90°, but is advantageously more than 90° to improve the fixation of the needle 210 within the septum, as the depth of septum material surrounding and fixing the needle increases with decreasing angle $\beta$ and, likewise, the securement afforded by the dermis 200 increases with such angles of attack, as does the ease with which the portion of the needle extending beyond the epidermis may be taped or otherwise secured to the epidermis.

Figure 3A:
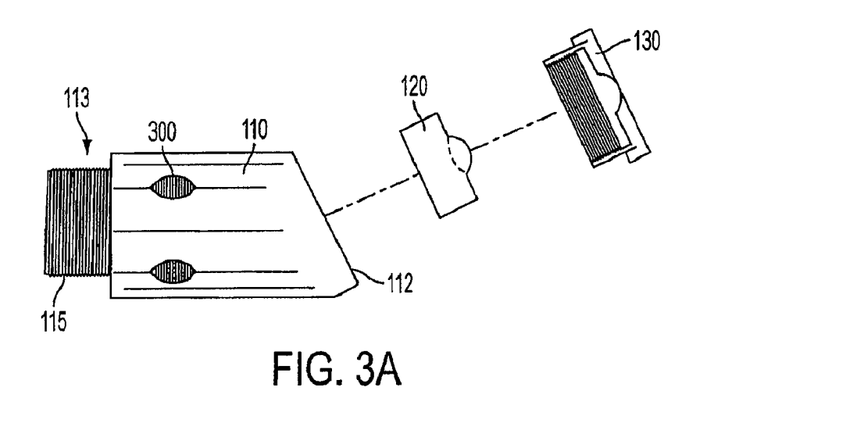
FIGS. 3(a)-(e) show side views depicting various stages of assembly of an example of a subcutaneous port in accord with the present concepts.
Figure 3B:
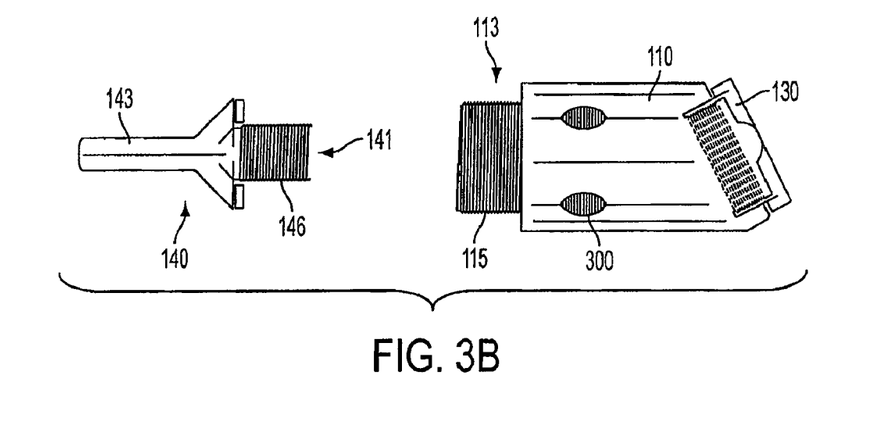
Figure 3C:
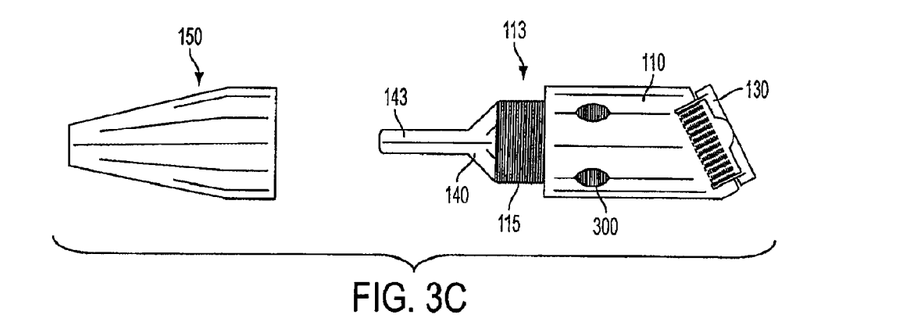
Figure 3D:
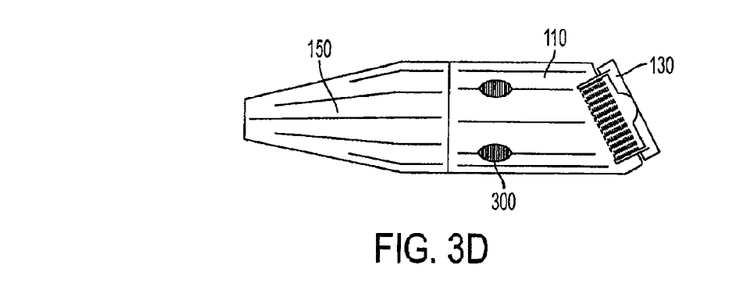

The port corpus 110 is, as shown in FIGS. 1(a)-(b) and 2, elongated about an axis (e.g., center axis C) and comprises an inlet 111 defining an inlet opening 112 at one end of the port corpus and an outlet 113 having an outlet opening 114 at a lengthwise opposing end of the port corpus. As shown in FIGS. 3(a)-3(c), the port corpus outlet 113 is annular and defines, by its interior surface, the outlet opening 114. A connecting member 116 such as, but not limited to, a thread is provided adjacent outlet opening 114. Connecting member 116 is configured to matingly and removably engage a corresponding thread or connecting member 146 provided on removable port conus inlet end 141. Port corpus outlet 113 also optionally includes a connecting member 115 provided adjacent an exterior surface of the port corpus outlet annulus for aspects of the port utilizing an optional removable casing 150, as shown in the illustrated examples. In the event that the removable casing 150 is not provided, the illustrated transitions, edges, and shoulders, would be preferably softened by rounding and by gradual transitions in diameter and a conventional catheter clamp provided to secure the catheter to the removable port conus 140.

Connecting member 115 may comprise, for example, a thread configured to matingly and removably engage a corresponding thread or connecting member 155 of the removable hollow casing 150. Port corpus 110 also comprises a connecting member (not shown) provided adjacent inlet opening 112, which connecting member comprises, in the illustrated example, a thread configured to matingly and removably engage a corresponding thread of removable septum retainer 130.

The removable conus 140 extends along the axis (e.g., center line C) and comprises an inlet end having an inlet opening 142 at one end and an outlet connector 143 having an outlet opening 144 at an opposing lengthwise end of. The removable conus inlet end 141 is an annulus in the illustrated example and serves to define inlet opening 142 as well as a portion of the channel 145 extending between the inlet opening and outlet opening 144. Channel 145 may be co-linear with center line C or may be displaced therefrom. The removable conus inlet end 141 comprises a connecting member adapted to co-act with a corresponding connecting member provided on or adjacent the port corpus outlet opening 114 or outlet 113.

As shown in FIG. 3(b), the removable conus inlet end 141 connecting member 146 is a thread configured to matingly and removably engage a corresponding connecting member (e.g., thread) provided adjacent an interior surface of port corpus outlet 113. In an alternative configuration, the inlet end 141 may comprise an annulus with inner and outer diameters larger than that of the illustrated example, with a corresponding reduction in the inner and outer diameters of the port corpus outlet 113 to permit mating and removable engagement between an connecting member (e.g., thread) on an outer surface of port corpus outlet 113 and a corresponding connecting member (e.g., mating thread) on an inner surface of inlet end 141. In this configuration, another connecting member (e.g. a thread) could be provide on an exterior surface of the inlet end 141 annulus to matingly and removably engage a corresponding connecting (e.g., a mating thread) of the removable hollow casing 150.

The removable connection provided between the removable conus inlet end 141 and the port corpus outlet opening 114 may be achieved by providing mating, removably engagable connecting members on respective portions of the removable conus inlet end and the port corpus outlet opening. In one aspect, a thread may be provide on an exterior surface of the removable conus inlet end 141 and a corresponding mating thread may be provided on an interior surface of the port corpus outlet opening 114. The threads may be configured to require multiple turns (i.e., multiple 360° revolutions) or only partial turns (e.g., a 270° rotation) to effect removal of the removable conus inlet end 141 from the port corpus outlet opening 114.

Other conventional mating, removably engagable connecting members may be used to connect the removable conus inlet 141 and the port corpus outlet 113 or outlet opening 114 (or any other removable connection between any other parts of the port 100) including, but not limited to any type of bayonet connectors, semi-turn connectors, multiple-turn connectors, and male/female connectors. For example, a resilient male connector could be provided on removable conus inlet end 141 and a female connector could be provided on port corpus outlet 113 with appropriate windows or openings provided in the port corpus outlet 113 to permit application of pressure to the male connector, such as by insertion of a key or device in such windows, to bias the male connector out of engagement with the female connector. These or other connection means can also be utilized for other port connections or connectors, such as for removable septum retainer 130. The availability of such alternate connecting members depends, practically, upon the type of connecting members and the size of the components bearing such connecting members, among other design factors. A port 100 configured used for drug delivery and/or sampling of a sheep jugular or carotid artery will present greater opportunity for variation in configuration than would, say, a port configured for use with a mouse lateral ventricle.

The subcutaneous port 100 port corpus 110, removable septum retainer 130, port conus 140, and removable hollow casing 150 are all made of conventional medically approved materials that engender minimal reaction from the body in which the port is implanted. These components may individually or collectively comprise or consist entirely of titanium, tantalum or a medically acceptable stainless steel material (e.g., 316L Grade SS). These components may also individually or collectively comprise or consist of any medical-grade metal or alloy, ceramic, plastic, or other medical-grade material presently known or which may be developed. For example, these components may comprise a relatively hard biocompatible non-metallic substance such as, but not limited to, Udel® Polysulfone made by Amoco Corp, a high density or ultra-high molecular weight polyethylene (HDPE/UHMW PE), or a pyrolytic carbon (PyC) such as the On-X® carbon made by Medical Carbon Research Institute (MCRI).

Titanium and tantalum are presently preferred metals, as these metals have a foreign body effect lower than that of stainless steels, which further reduces the susceptibility of tissues to infection. Additionally, such materials facilitate sterilization (e.g., thermo-sterilization) and re-use of the port 100 constituent components (port corpus 110, removable septum retainer 130, port conus 140, and removable hollow casing 150).

Septum 120 is affixed wholly or partially within the removable septum retainer 130 and/or between the removable septum retainer and inner surfaces of the port corpus 110. In the example of FIGS. 1(a)-3(e), the removable septum retainer 130 is removably inserted into the port corpus inlet opening 112 so as to dispose the septum 120 in a position to occlude the port corpus inlet opening. In this example, the removable septum retainer 130 comprises a flanged annulus having threads provided on an exterior surface of such annulus. In such aspect, the port corpus inlet opening 112 inner surface comprises a corresponding mating thread. Alternatively, the flanged annulus may have threads provided on an interior surface of such annulus and outwardly disposed surfaces of the port corpus inlet 111 may comprise a corresponding mating thread. As noted above, the threads may be configured to require multiple turns (i.e., multiple 360° revolutions) or only partial turns (e.g., a 270° rotation) to effect removal of the removable septum retainer 130 from the port corpus inlet 111 or inlet opening 112. As further noted above, other conventional removably engagable arrangements may be advantageously implemented in accord with the present concepts.

As shown, the septum 120 is substantially housed within the annulus of the removable septum retainer 130. In alternate configurations, the removable septum retainer 130 may comprise an annulus which only partially houses the septum 120 or may comprise an internally threaded annulus adapted for attachment to a thread provided on an exterior surface of port corpus inlet 111 so as to provide only a ring to act upon an outer surface of septum 120.

Septum 120 is configured to substantially prevent leakage from the subcutaneous port 100 over prolonged use of the port. Suitable septum 120 materials include silicone elastomers such as, but not limited to polyurethane elastomers, polysulfide elastomers, and those manufactured by Dow Corning Corporation of Midland, Mich. (e.g., Dow Corning Q7-4735), Nusil Technology Company's MED-4735, and a composition sold under the trade name "Silastic". Other medically acceptable elastomeric materials may also be employed. Further, septum 120 may include a single material, as described above, or may be a composite material or a plurality of stacked or laminated layers of one or more materials. In the example of FIGS. 1(a)-2, the thickness of the septum 120 is about 3.5 mm and the diameter is about 6 mm, but may be thicker, thinner, larger or smaller in accord with the particular application and species.

Septum 120 is preferably maintained in a compressed state to enhance resealability. This compressed state is achieved, in one aspect, by selecting the septum 120 volume to be somewhat larger than the space in which the septum is permitted to occupy, such as by making the septum diameter and/or thickness slightly larger than corresponding dimensions of the connection between the removable septum retainer 130 inner annular surface and port corpus inlet 111. The resulting interference fit provides reliable a fluid-tight seal about a circumference of septum 120.

It is preferred to use a non-coring needle 210. Depending on the particular application, as noted above, needles 210 ranging from about 20 to 27-gauge may be used (i.e., 20-gauge for large port septums and 27-gauge for small port septums) to facilitate resealability of the septum 120 following withdrawal of the needle.

A chamber 160 is defined between the inlet 111 or the inlet opening 112 and the outlet 113 or the outlet opening 114 and more particularly between the septum inner surface 121 and the removable conus 140 inlet end 141, which is removably inserted into the port corpus outlet opening 114. Chamber 160 temporarily stores and/or facilitates flow of a drug or other fluid injected therein for controlled release therefrom through the port conus 140 channel 145.

As noted above, an outer surface of the removable hollow casing 150 is preferably substantially curvilinear in a cross-section taken along the axis and is frustoconical along at least a portion of its length along the axis. The outer surface of the removable hollow casing 150 is preferably substantially flush with the outer surface of the port corpus 110 at the connection therebetween with minimal, if any, interstices.

Figure 3E:
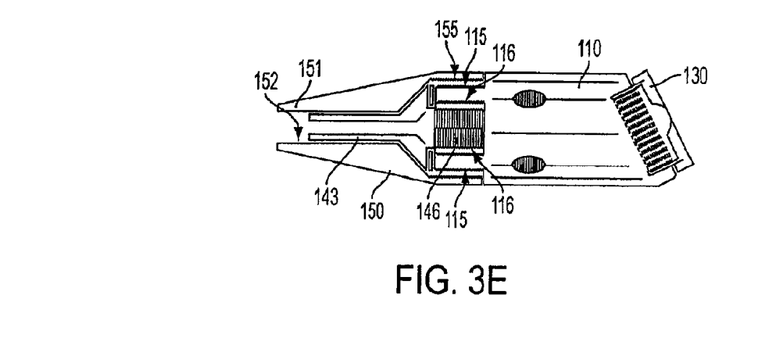
Figure 4A:
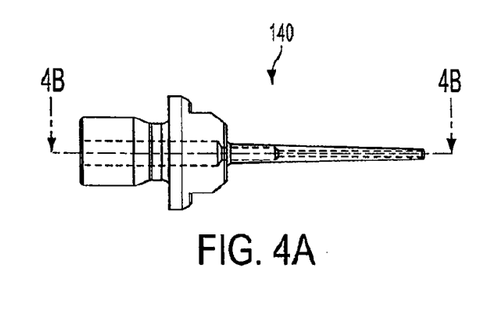
FIGS. 4(a)-4(b) respectively show a side view and a cross-sectional view of another example of a port conus in accord with the present concepts.
Figure 4B:
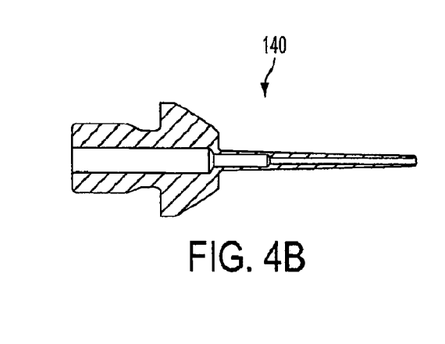
Figure 5A:
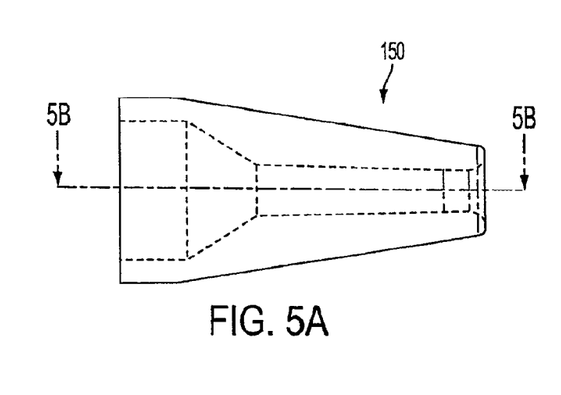
FIGS. 5(a)-5(b) respectively show a side view and a cross-sectional view of another example of a hollow casing in accord with the present concepts.
Figure 5B:
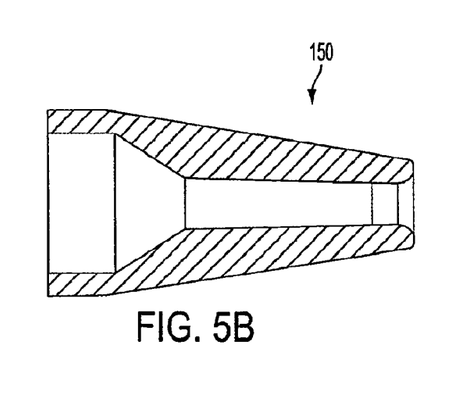
Figure 6A:
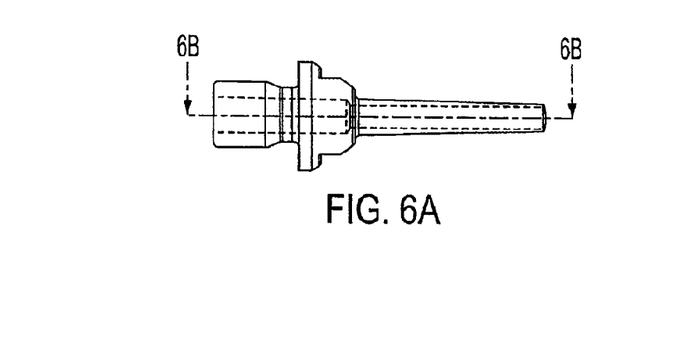
FIGS. 6(a)-6(b) respectively show a side view and a cross-sectional view of still another example of a port conus in accord with the present concepts.
Figure 6B:
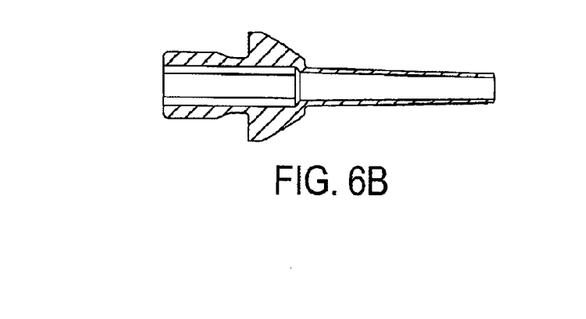
Figure 7A:
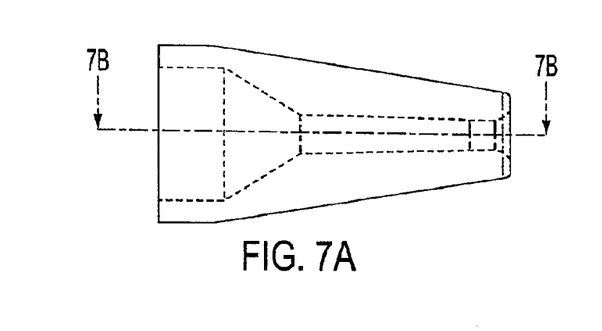
FIGS. 7(a)-7(b) respectively show a side view and a cross-sectional view of still another example of a hollow casing in accord with the present concepts.
Figure 7B:
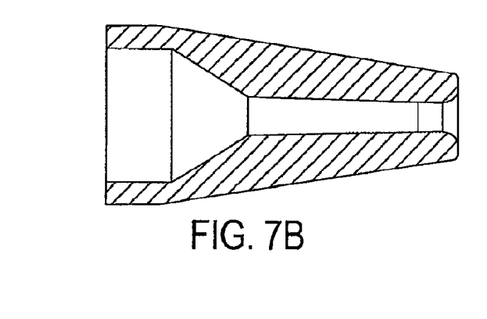

The interior surface 152 of the removable hollow casing 150 is, as shown in FIG. 3(e), configured to define a gap between an exterior surface of the removable conus outlet connector 143 along at least a portion of the length of the removable hollow casing. This gap corresponds substantially to a wall thickness of a catheter so as to permit securement of a catheter 220 between at least a portion of an exterior surface of the removable conus outlet connector 143 and an opposing interior surface 152 of removable hollow casing 150, as shown in FIG. 1(b). For example, if a French size 1 silicon or polyurethane catheter were used, the outside diameter of the catheter would be 0.4 mm and the minimal diameter of the removable hollow casing 150 interior surface 152 would corresponding be about 0.4 mm. The inner diameter of such catheter is 0.1 mm. Therefore, the outer diameter of the removable conus outlet connector 143 would be about 0.1 mm and the aforementioned gap would be about 0.3 mm in this example. Similarly, a French size 9 catheter (OD of 3.2 mm, ID of 1.6 mm) requires a gap of about 1.6 mm.

In the illustrated examples of FIGS. 1(a)-3(e), the outlet end 151 of the removable hollow casing 150 extends beyond the outlet opening 144 of the removable conus outlet connector 143 along the axis. This overlap is provided to prevent inadvertent damage to the connection between a catheter and the removable conus outlet connector 143 which may be caused by direct contact with the connection during implantation or during manual fixation of the port 100 prior to a drug injection or fluid withdrawal from the port. Further, the removable hollow casing 150 positively fixes the catheter within the body of the port 100, preferably along substantially an entire length of the removable conus outlet connector 143, so as to provide an extensive area over which tensile or compressive forces transmitted to the connection Apertures 300 are provided on exterior surfaces of the port 100, such as shown in FIGS. 3(a)-3(e), to facilitate connection of the port to the underlying fasia 400 by an appropriate ligature 410, such as shown in the cross-sectional view of FIG. 1(b). In one aspect, apertures are provided on opposing sides of the port.

FIGS. 4(a)-(b) and 5(a)-(b) respectively show side and cross-sectional views of one example of port conus 140 and hollow casing 150 provided in accord with the concepts disclosed herein.

FIGS. 6(a)-(b) and 7(a)-(b) respectively show side and cross-sectional views of another example of port conus 140 and hollow casing 150 provided in accord with the concepts disclosed herein.

Figure 8A:
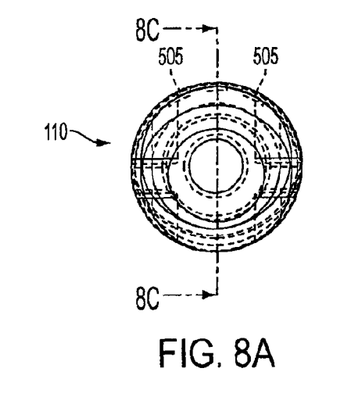
FIGS. 8(a)-8(c) respectively show a front, a top, and a cross-sectional view of another example of a port corpus in accord with the present concepts.
Figure 8B:
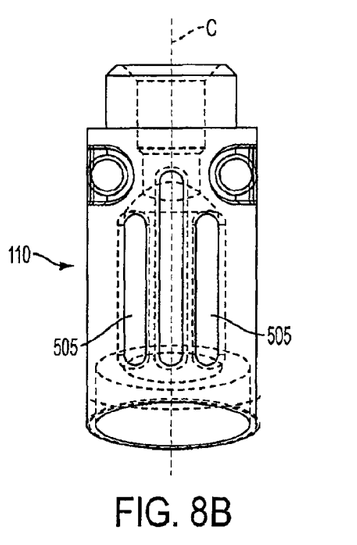
Figure 8C:
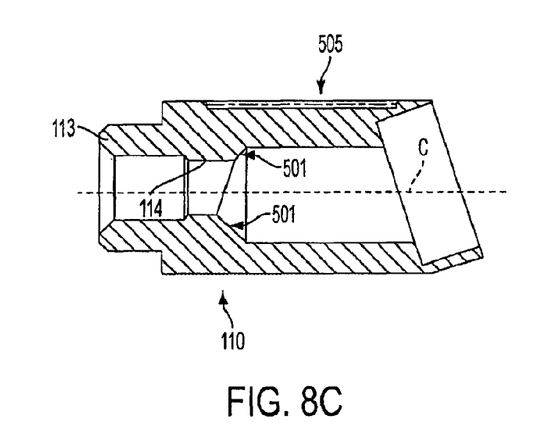

FIGS. 8(a)-(c) show front, top, and longitudinal cross-sectional views of a port corpus 110 adapted for use with the port conus 140 and hollow casing 150 presented in FIGS. 4(a)-7(b) in accord with the present concepts. The port corpus 110 depicted in the example of FIGS. 8(a)-(c) has a chamber 160, port corpus outlet opening 114, and port corpus outlet 113 with a configuration different than that of the example shown in FIG. 1(a). In the example of FIGS. 8(a)-(c), the port corpus 110 chamber 160 has a distal wall 501 and port corpus outlet opening 114 which is not symmetric about the center axis C. In the example shown in FIG. 8(c), port corpus outlet opening 114 has a centerline C2 which is displaced upwardly from the centerline of the port corpus 110 by about 0.4 mm. Distal wall 501 of chamber 160 is advantageously angled inwardly away from the septum or curved to mitigate or prevent fluid stagnation in the chamber.

Another feature shown in FIGS. 8(a)-(c) are the longitudinal depressions 505 provided on a top portion of port corpus 110. The longitudinal depressions 505 ease handling and manipulation of the subcutaneous port 100 and resist circulation or rotation of the port about a longitudinal axis of the port. A greater or lesser number of longitudinal depressions 505 may be provided on the top portion of port corpus 110 or on any other outer surface of port corpus 110 (e.g., bottom or side portions). The longitudinal depressions 505 may be continuous, as shown, or may comprise intermittent depressions, which may be oval, circular, or other configuration, disposed along a longitudinal axis. For example, the longitudinal depressions 505 may be approximated by a plurality of oval or circular depressions arranged in a line. It is preferred that all edges of the depressions be rounded. Alternatively, the longitudinal depressions 505 could be replaced with rounded longitudinal protrusions 505.

Figure 9A:
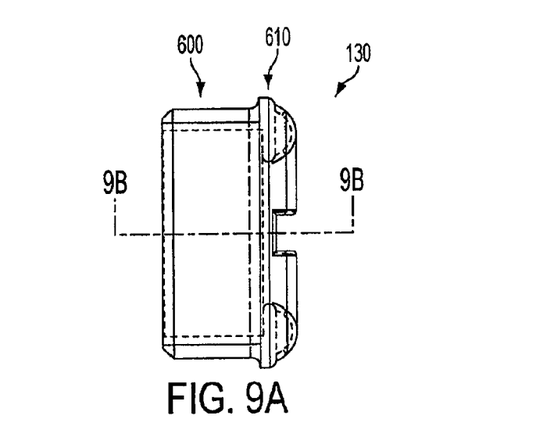
FIGS. 9(a)-9(c) respectively show a side, a cross-sectional, and a front view of another example of a removable septum retainer in accord with the present concepts.
Figure 9B:
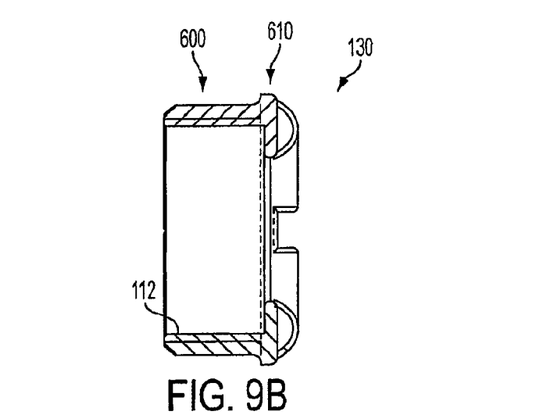
Figure 9C:
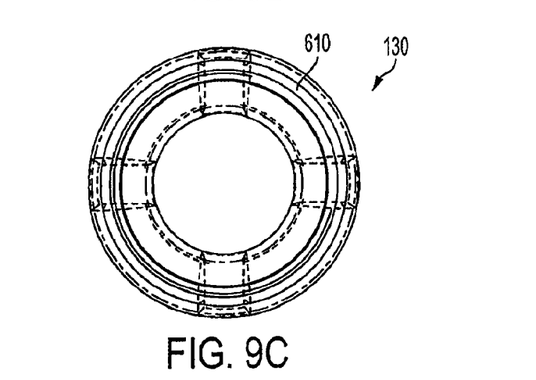

FIGS. 9(a)-(c) shows one example of a removable septum retainer 130. The removable septum retainer 130 possesses a threaded outer surface configured for connection to a corresponding thread or threads on inner surfaces of port corpus 110. Septum retainer 130 comprises a flanged annulus having a cylindrical portion 600 and a flange portion 610. The flange portion 610 has torquing features 620 (e.g., slots) formed in a top portion thereof to permit engagement of a torque producing tool (e.g., a flat head medical screwdriver) and a corresponding application of a torque to screw in or remove the septum retainer 130 from the port corpus 110. Alternate torquing features 620 could also be provided (e.g., holes) for use with any variety of torque producing tool to permit insertion and/or removal of septum retainer 130. In accord with other configurations, such as noted above, wherein connections other than threaded connections are provided, the flange portion 610 is preferably provided with a means by which an appropriate force (e.g., a force along a longitudinal axis of the port 100) may be provided to connect or disconnect the connectors. For example, if a bayonet or male/female connector is used to connect septum retainer 130 to the port corpus 110, threaded holes may be disposed on the flange portion 610 top portion at opposing sides of the septum opening to permit insertion of threaded gripping means into such threaded holes to permit application of a force along a longitudinal axis of the port 100 to insert or remove the septum retainer.

As shown, the septum 120 is substantially housed within the annulus of the removable septum retainer 130. In alternate configurations, the removable septum retainer 130 may comprise an annulus which only partially houses the septum 120 or may comprise an internally threaded annulus adapted for attachment to a thread provided on an exterior surface of port corpus inlet 111 so as to provide only a ring to act upon an outer surface of septum 120.

In accord with the present disclosure, a method of preparing for implantation a subcutaneous port 100 is described below. As noted above, one object of the disclosed port is to provide an improved port for use with humans or with feril animals, experimental animals, or domestic animals, such as but not limited to mice, rats, rabbits, dogs, cats, sheep, and primates, to facilitate continuous or intermittent drug and/or fluid administration and/or withdrawal therefrom. The steps below reflect one exemplary sequence of steps, but various steps may be performed in alternate orders as can be appreciated by one of ordinary skill in the art.

The initial step comprises selection of a port corpus 110, a removable septum retainer 130, a septum 120, a removable conus 140, and a catheter for assembly to accomplish a desired objective. It is also preferred, but not necessary, that a removable hollow casing 150 also be selected and deployed in conjunction with the remainder of the port 100. Septum 120 is disposed between the port corpus inlet opening 112 and septum retainer 130 to occlude the port corpus inlet opening and the septum retainer 130 is then removably connected to the port corpus 110 on one end using the respective connecting members (e.g., threads). The removable conus 140 is connected to the port corpus 110 on another end using the respective connecting members (e.g., threads) 146, 116. The selected catheter is then connected to the removable conus outlet connector 143, preferably after a distal end of the catheter has already been placed in a desired position. If the removable hollow casing 150 is to be used, such casing is then connected to the port corpus outlet 113 using the respective connecting members (e.g., threads) 115, 155.

The subcutaneous port 100 in accord with the present concepts also permits surgical replacement of a septum 120 in an implanted subcutaneous port. This procedure requires selection of a replacement septum 120, accessing the implanted subcutaneous port, removal of the removable septum retainer 130 from the port corpus 110 by disconnecting the respective connecting members, examples of which are provided above (e.g., by unscrewing the threaded connection), removal of the old septum, placement of the replacement septum between the port corpus inlet opening 112 and the removable septum retainer to occlude an inlet opening of the port corpus, and connection of the removable septum retainer to the port corpus by using the respective connecting members (e.g., by screwing together the threaded parts). Explantation or removal of the port 100 is not required for this procedure, which correspondingly leaves the catheter and port undisturbed to the benefit of the animal or patient.

One advantage of the presently disclosed subcutaneous port 100 is that the port may be explanted, the septum removed, the remaining components completely cleaned and sterilized, a new septum installed and placed back in service in the same or a different subject or patient. If an optional washer 350 comprising titanium, tantalum, or a surgical grade stainless steel is used, such as shown in FIG. 3(b), it is preferably discarded and replaced with a new washer. Thus, the port may be quickly and efficiently placed back in service following use.

Further, the parts may be configured to be interchangeable so that for a particular port corpus 110 size, a variety of removable port conus 140 sizes are available having different channel sizes or configurations (to control flow) or different outlet connector 143 sizes to permit connection of different gauge catheters for different applications (e.g., an individual port conus for each of French sizes 1-9). The connecting members, which are all threaded connectors in the illustrated examples, facilitate interchangeability of parts. This permits the port to be used in a multitude of applications including intravascular, intrathecal, and intraventrical applications, as well as a multitude of species.

The removable hollow housing 150 may have an inner surface 152 which is mated to a particular port conus outlet connector size or a particular combination of port conus outlet connector and catheter thickness. Alternately, the removable hollow housing 150 may have an inner surface 152 adapted, such as by a progressively stepped inner surface defining a larger opening toward the removable hollow casing outlet 151 and smaller openings toward the connection between the casing and the port corpus 110.

The cross-section permits implantation of the device 100 with minimal tissue damage, as a smaller opening in the tissue is required than for conventional subcutaneous ports which possess lateral protuberances. Specifically, the incidence of post-operative infection is related to the amount of local damage caused during surgery, as increasing levels of tissue trauma caused by surgery increasingly compromise local vascular supplies to the soft tissues, which results in local tissue ischemia (insufficient oxygen to tissues) and predisposes the tissues to bacterial growth and sepsis. Thus, minimally invasive procedures, such as that permitted by the slender shape of the disclosed subcutaneous port 100, have a positive effect on healing. Excessive tension on wound edges also increases ischemia. Wound edge tension is minimized by the slender shape of the disclosed subcutaneous port 100. These benefits provided by the disclosed subcutaneous port 100 are particularly pronounced in small animals, such as mice.

Once implanted, the disclosed subcutaneous port 100 provides continuous access to internal regions of the body without requiring additional needle penetrations directly into these regions. Instead a catheter is optionally provided to extend from the subcutaneous port 100 to the site of interest where the catheter serves as a continuously-available conduit. A needle need only be placed in fluid communication with the subcutaneous port 100 chamber 160 to respectively inject, withdraw or mix fluids from or to the site of interest, as applicable for a desired application and selected combination of components.

Figure 10:
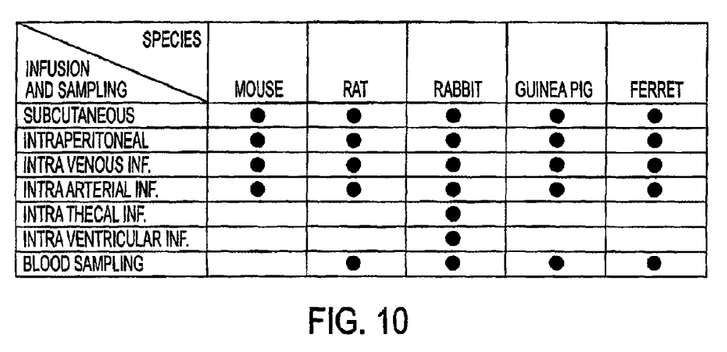
FIG. 10 shows a chart of exemplary uses to which the disclosed port may be implemented in accord with the present concepts.

To illustrate the versatility of the disclosed modular port-catheter system, which is configurable to include access to all vessels, chambers, and cavities of a body for which catheter diameters from 3 to 7 French (e.g., about 0.9 mm OD to 2.4 mm OD, which generally corresponds to a range of 20-gauge to 13-gauge catheters) are needed, FIG. 10 presents exemplary, non-limiting uses in which the disclosed modular port-catheter system may be advantageously implemented in accord with the present disclosure. Alternatively, the disclosed modular port-catheter system may be configured for use with catheter diameters of 1 or 2 French (e.g., about 0.4 mm OD to 0.6 mm OD) or up to 9 French (3.2 mm OD).

The purpose of the above description and examples is to illustrate some aspects of the present disclosure without implying any limitation. It will be apparent to those skilled in the art that various modifications and variations may be made to the device and method of the present disclosure without departing from the spirit or scope thereof. For example, despite the obvious advantages provided by the disclosed subcutaneous port 100, which is modular or multi-functional, the overall profile of the subcutaneous port is itself advantageous for the reasons disclosed and the present concepts expressly include unitary preconfigured subcutaneous ports (i.e. non-modular or urn-functional) having the overall shape of the disclosed subcutaneous port. For example, the disclosed subcutaneous port may be provided in a disposable form with a pre-selected and pre-configured catheter and septum so that surgeons, veterinarians, or lab technicians do not have to assemble the subcutaneous port.

I claim:

1. A subcutaneous port comprising:
a port corpus elongated and centered about an axis and comprising an inlet defining an opening at one end of the port corpus, an outlet having an outlet opening at a lengthwise opposing end of the port corpus, and a chamber defined therebetween, one of the inlet and the inlet opening comprising a first connecting member and one of the outlet and the outlet opening comprising a second connecting member, the inlet opening and the outlet opening being the only openings of the port corpus in communication with the chamber;
a septum;
a removable septum retainer comprising a third connecting member being removably engaged with the first connecting member so as to dispose the septum in a position to occlude the port corpus inlet opening; and
a removable conus co-axial with the port corpus, the removable conus comprising an inlet end having an inlet opening at one end of the removable conus, an outlet connector having an outlet opening at an opposing lengthwise end of the removable conus, and a channel extending therebetween, the removable conus inlet end further comprising a fourth connecting member being removably engaged with the second connecting member,
wherein the port corpus inlet is canted inwardly along the axis of the port corpus; and
wherein the port corpus, septum, septum retainer, and conus are engageable to form a port assembly having a substantially slender overall profile for implantation under the skin of an animal.

2. A subcutaneous port according to claim 1,
wherein the axis is a central axis common to the port corpus and the removable conus.

3. A subcutaneous port according to claim 1, further comprising:
a fifth connecting member provided adjacent an exterior surface of one of the removable conus and the port corpus; and
a removable hollow casing extending along the axis, the removable hollow casing comprising a sixth connecting member being removably engaged with the fifth connecting member.

4. A subcutaneous port according to claim 3,
wherein the removable septum retainer comprises a flanged annulus, and
wherein the septum is disposed at least partially within the removable septum retainer annulus.

5. A subcutaneous port according to claim 4,
wherein an outlet end of the removable hollow casing extends beyond the outlet opening of the removable conus outlet connector.

6. A subcutaneous port according to claim 4,
wherein an outer surface of each of the port corpus and the removable casing is substantially curvilinear in a cross-section taken along the axis.

7. A subcutaneous port according to claim 4,
wherein an outer surface of each of the port corpus and the removable casing is one of substantially circular and substantially elliptical in a cross-section taken along the axis.

8. A subcutaneous port according to claim 4,
wherein the port corpus inlet opening first connecting member comprises a thread formed on an interior surface of the inlet opening,
wherein the removable septum retainer third connecting member comprises a thread formed on an exterior surface of the flanged annulus, and
wherein the first connecting member thread and the third connecting member thread are matingly engageable.

9. A subcutaneous port according to claim 4,
wherein a distal wall of the chamber is angled inwardly, away from the septum.

10. A subcutaneous port according to claim 9,
wherein the port corpus outlet comprises an annulus, an interior surface of the annulus defining the outlet opening,
wherein the second connecting member comprises a thread formed adjacent the interior surface of the annulus,
wherein the removable conus inlet comprises an annulus, an interior surface of the annulus defining a portion of the channel and an exterior surface bearing the fourth connecting member, the fourth connecting member comprising a thread,
wherein the fifth connecting member comprises a thread formed adjacent an exterior surface of the port corpus outlet annulus,
wherein the sixth connecting member comprises a thread formed adjacent an interior surface of the removable hollow casing,
wherein the second connecting member thread and the fourth connecting member thread are matingly engageable, and
wherein the fifth connecting member thread and the sixth connecting member thread are matingly engageable.

11. A subcutaneous port according to claim 10, further comprising:
a catheter attached to the removable conus outlet connector.

12. A subcutaneous port according to claim 4,
wherein a distal wall of the chamber is curved at at least upper and lower extents thereof.

13. A subcutaneous port according to claim 3,
wherein a gap is defined between an exterior surface of the removable conus outlet connector and an opposing interior surface of the removable hollow casing, and
wherein the gap corresponds substantially to a wall thickness of a catheter so as to permit securement of a catheter between at least a portion of an exterior surface of the removable conus outlet connector and an opposing interior surface of the removable hollow casing.

14. A subcutaneous port according to claim 13,
wherein an outer surface of the port corpus is substantially cylindrical along the axis and wherein an outer surface of the removable casing is frustoconical along at least a portion thereof along the axis.

15. A subcutaneous port according to claim 14,
wherein the port corpus inlet is canted inwardly with respect to the port corpus within a range between 20° and 70°.

16. A subcutaneous port according to claim 15,
wherein each of the port corpus, removable port conus, removable septum retainer, and removable hollow casing comprises at least one of a surgical grade stainless steel, titanium, and tantalum.

17. A subcutaneous port according to claim 1, further comprising:
a catheter attached to the removable conus outlet connector.

18. A method comprising the steps of:
selecting a port corpus, a removable septum retainer, a septum, a removable port conus, and a catheter for assembly, the port corpus, septum, septum retainer, and conus being connectible to form a port assembly having a substantially slender overall profile for implantation under the skin of an animal, said port corpus being elongated and centered about an axis and comprising an inlet defining an opening at one end of the port corpus, an outlet having an outlet opening at a lengthwise opposing end of the port corpus, and a chamber defined therebetween, one of the inlet and the inlet opening comprising a first connecting member and one of the outlet and the outlet opening comprising a second connecting member, the inlet opening and the outlet opening being the only openings of the port corpus in communication with the chamber, said removable septum retainer comprising a third connecting member being removably engaged with the first connecting member so as to dispose the septum in a position to occlude the port corpus inlet opening; said removable conus co-axial with the port corpus, extending along the axis, the removable conus comprising an inlet end having an inlet opening at one end of the removable conus, an outlet connector having an outlet opening at an opposing lengthwise end of the removable conus, and a channel extending therebetween, the removable conus inlet end further comprising a fourth connecting member being removably engaged with the second connecting member, and said port corpus inlet being canted inwardly along the axis of the port corpus;

disposing the septum between the port corpus inlet opening and the removable septum retainer to occlude an inlet opening of the port corpus;

connecting the removable septum retainer to the port corpus by connecting the first connecting member to the third connecting member;

connecting the removable conus to the port corpus by connecting the fourth connecting member and the second connecting member; and connecting the catheter to the removable conus outlet connector.

19. A method in accord with claim 18 comprising the steps of:

making an incision in the skin of the animal;
inserting the subcutaneous port beneath the skin;
positioning a distal end of the catheter at a predetermined site within the animal; and
closing the incision.

20. A method in accord with claim 19, wherein said animal is a rodent.

21. A method in accord with claim 20, wherein said step of making an incision in the skin of the animal comprises making an incision in the skin of the rodent in one of a posterior dorsal location, a posterior lateral location, and a posterior ventral location.

22. A method in accord with claim 21, wherein said step of making an incision in the skin of the animal comprises making an incision in the skin of the rodent in a generally posterior dorsal location with at least a portion of the incision disposed adjacent a base of the tail, and wherein said step of inserting the subcutaneous port beneath the skin comprises inserting the subcutaneous port with the septum adjacent the base of the tail.

23. A method comprising the steps of:

selecting a port corpus, a removable septum retainer, a septum, a removable port conus, a removable hollow casing, and a catheter for assembly, the port corpus, septum, septum retainer, conus and casing being connectible to form a port assembly having a substantially slender overall profile for implantation under the skin of an animal;

said port corpus being elongated about an axis and comprising an annular inlet defining an opening at one end of the port corpus, an annular outlet having an outlet opening at a lengthwise opposing end of the port corpus, and a chamber defined therebetween, the inlet opening and the outlet opening being the only openings of the port corpus in communication with the chamber, said port corpus further comprising a first threaded connection on an interior surface of the inlet opening, a second threaded connection on an interior surface of the outlet opening, and a fifth threaded connection on an exterior surface of the port corpus annular outlet;

said removable septum retainer comprising a flanged annulus and a third threaded connection formed on an exterior surface of the flanged annulus to matingly engage the first threaded connection so as to dispose the septum in a position to occlude the port corpus inlet opening;

said removable port conus extending along the axis, the removable conus comprising an annular inlet end having an inlet opening at one end of the removable conus, an outlet connector having an outlet opening at an opposing lengthwise end of the removable conus, and a channel extending therebetween, the removable conus inlet end further comprising a portion of said channel defined by an interior surface thereof and a fourth threaded connection on an exterior surface thereof which is removably engageable with the second threaded connection, and said port corpus inlet being canted inwardly along the axis of the port corpus; and said removable hollow casing extending along the axis, the removable hollow casing comprising a sixth threaded connection formed on an interior surface of the removable hollow casing to be removably engageable with the fifth threaded connection;

disposing the septum between the port corpus inlet opening and the removable septum retainer to occlude an inlet opening of the port corpus;

connecting the removable septum retainer to the port corpus by screwing the first connecting member and the third connecting member together;

connecting the removable conus to the port corpus by screwing the fourth connecting member and the second connecting member together;

connecting the catheter to the removable conus outlet connector, and connecting the removable hollow casing to the port corpus by screwing the fifth connecting member and the sixth connecting member together.

24. A method in accord with claim 23 comprising the steps of:

making an incision in the skin of the animal;
inserting the subcutaneous port beneath the skin;
positioning a distal end of the catheter at a predetermined site within the animal; and
closing the incision.

25. A method in accord with claim 24, wherein said animal is a rodent.

26. A method in accord with claim 25, wherein said step of making an incision in the skin of the animal comprises making an incision in the skin of the rodent in a generally posterior dorsal location.

27. A method in accord with claim 26, wherein said step of making an incision in the skin of the animal comprises making an incision in the skin of the rodent in a generally posterior dorsal location with at least a portion of the incision disposed adjacent a base of the tail, and wherein said step of inserting the subcutaneous port beneath the skin comprises inserting the subcutaneous port with the septum adjacent the base of the tail.

28. A method for implanting an elongate subcutaneous port according to claim 1 into a rodent comprising the steps of:

making at least one of a longitudinal and a transverse incision in the skin of the rodent in a generally posterior dorsal location with at least a portion of the incision disposed adjacent a base of the tail,     inserting the subcutaneous port beneath the skin with a septum borne by the elongate subcutaneous port being disposed adjacent the base of the tail;

positioning a distal end of a catheter borne by the elongate subcutaneous port at a predetermined site within the animal; and     closing the incision.

* * * * *